(12) United States Patent
Golz-Berner et al.

(10) Patent No.: US 6,426,080 B1
(45) Date of Patent: Jul. 30, 2002

(54) COSMETIC PREPARATION OF ACTIVE SUBSTANCES WITH HIGH PROTECTION FACTOR AGAINST FREE RADICALS

(75) Inventors: Karin Golz-Berner; Leonhard Zastrow, both of Monaco (MC)

(73) Assignee: Coty, B.V., Haarlem (NL)

( * ) Notice: Subject to any disclaimer, the term of this patent is extended or adjusted under 35 U.S.C. 154(b) by 0 days.

(21) Appl. No.: 09/720,335

(22) PCT Filed: Jun. 22, 1999

(86) PCT No.: PCT/DE99/01851
§ 371 (c)(1),
(2), (4) Date: Dec. 22, 2000

(87) PCT Pub. No.: WO99/66881
PCT Pub. Date: Dec. 29, 1999

(30) Foreign Application Priority Data

Jun. 24, 1998 (DE) ......................................... 198 30 004
Dec. 23, 1998 (DE) ......................................... 198 60 754

(51) Int. Cl.[7] ........................... A61K 6/00; A61K 31/74; A01N 37/18; A01N 25/00
(52) U.S. Cl. ................. 424/401; 424/78.03; 424/78.05; 514/2; 514/946
(58) Field of Search .............................. 424/401, 78.03, 424/78.05, 725, 195.17, 195.16, 195.15; 514/2, 788.1, 844–848, 873, 886–87, 904, 905, 937, 944, 945, 946–47

(56) References Cited

U.S. PATENT DOCUMENTS

| | | | |
|---|---|---|---|
| 4,402,856 A | | 9/1983 | Schnoring et al. |
| 5,626,015 A | * | 5/1997 | Ribier et al. ................. 424/450 |
| 5,629,185 A | | 5/1997 | Stanzl et al. |
| 5,686,405 A | * | 11/1997 | Lebreton et al. ....... 424/195.15 |
| 5,716,599 A | | 2/1998 | Golz et al. |
| 5,759,969 A | * | 6/1998 | Tsaur et al. .................. 510/158 |
| 5,804,168 A | * | 9/1998 | Murad .......................... 424/59 |
| 5,916,577 A | | 6/1999 | Golz et al. |

FOREIGN PATENT DOCUMENTS

| | | |
|---|---|---|
| DE | 34 03 476 | 8/1984 |
| DE | 42 31 544 | 2/1994 |
| DE | 43 28 639 | 3/1995 |
| DE | 42 31 543 | 6/1995 |
| DE | 196 53 736 | 6/1998 |
| EP | 0 507 272 | 4/1992 |
| EP | 0 707 844 | 4/1995 |
| EP | 0 768 079 | 4/1997 |
| FR | 2 597 337 | * 1/1987 |
| FR | 2 770 228 | * 10/1997 |
| JP | 58-26809 | * 2/1983 |
| JP | 8-301722 | * 8/1996 |
| JP | 09291023 | 11/1997 |
| WO | 93 24106 | 12/1993 |
| WO | 96 06532 | 3/1996 |
| WO | 97/45100 | 12/1997 |

OTHER PUBLICATIONS

JPO Abstract, JP408301722A, Aug. 1996.*
Machine translation, JP408301722A, Aug. 1996.*
SU 1780753A1, Kolinko et al., Derwent Abstract, Dec. 1992.*
JP58026809A, Derwent Abstract, Feb. 1983.*
Compton's Encyclopedia Online v3.0, ©1998.*
FR002770228A1, Abstract, Oct. 1997.*
FR 2597337A, Derwent Abstract, Jan. 1987.*

* cited by examiner

Primary Examiner—Michael G. Hartley
Assistant Examiner—Michael A. Willis
(74) Attorney, Agent, or Firm—Collard & Roe, P.C.

(57) ABSTRACT

The disclosed cosmetic preparation of active substances protects the skin in a particularly effective way against free radical aggression, both alone and in combination with other active substances. The preparation consists of a Quebraco blanco bark extract containing at least 90 wt. % proanthocyanidin oligomers, a silkworm extract containing the peptide cecropin, amino acids and a vitamin mixture, a non-ionic, cationic or anionic hydrogel, phospholipids and water, and may also contain further active substances such as vitamin derivatives and plant extracts of acerola, sea weed, citrus, bitter orange, cherry, papaya, tea, coffee beans, Mimosa tenuiflora and angelica. The preparations have protection factors against free radicals of up to 10000, and the cosmetic compositions containing these preparations have protection factors of between 40 and 200, depending on their proportion of the preparations.

12 Claims, No Drawings

COSMETIC PREPARATION OF ACTIVE SUBSTANCES WITH HIGH PROTECTION FACTOR AGAINST FREE RADICALS

The disclosed cosmetic preparation of active substances protects the skin in a particularly effective way against free radical aggression, both alone and in combination with other active substances.

Free radicals such as superoxide ions, hydroxy radicals, oxides are known as a major factor of degeneration and thus the ageing of the skin. They destruct the proteins and lipids of the cellular membrane, affect the DNA and also decompose the hyaluronic acid, a key substance of the skin. Under normal biological conditions there is an equilibrium ratio between the free radicals coming up and their embankment by endogenous chemical or enzymatic systems. Additional outside stress factors such as aggressive atmosphere, tobacco smoke, ultraviolet radiation etc. may overload these inherent immune systems and shift the equilibrium in favour of the free radicals. Inflammation or ageing phenomena of the skin may occur, indicating a need for compensation by cosmetic products.

There has already been proposed a series of products for this purpose, most of them containing mixtures of the vitamins A, C and E or additives of superoxide dismutase or extracts of certain plants or animals. Thus a cosmetic compound containing ultrasound decomposition products of yeast and other cellular dispersions is known from U.S. Pat. No. 5,629,185. From WO96/29048 a cosmetic containing condensed decomposition products of plants or animals is known. There is also a number of publications describing the use of pure plant extracts for cosmetic purposes, such as WO97/45100, where a mixture of seven different extracts is described for anti-cellulite treatment.

The search for other effective substances is a major element of cosmetic research. Another problem of many of these products is that the substances which are effective against free radicals often do not keep their catching properties within the ready cosmetic compound, i.e. it requires special formulations to permanently maintain the effectiveness of the radical catchers.

On the other hand it seems that it has not become widely known in the cosmetic industry yet that there is a possibility of measuring the antioxidant potential of the skin (DE 4328639) and recently also of determining the radical protection coefficient of a cosmetic preparation by using a relatively simple method and to purposefully add materials to such a preparation.

It is an object of the present invention to provide a cosmetic preparation of active substances which has a particularly high radical protection potential.

Another objective of the invention is to provide a preparation of active substances that keeps its radical protection potential over a long period of time.

Another objective of the invention is to provide special cosmetic compounds containing this preparation of active substances and especially such preparations of active substances which achieve further improvement of properties, in particular with regard to opening the pores of the skin.

According to the invention, the cosmetic preparation of active substances with a high radical protection factor is characterised by comprising (a) a product obtained by extraction of the bark of *Quebracho blanco* and subsequent enzymatic hydrolysis, containing at least 90 percent by weight of proanthocyanidine oligomers and up to 10 percent by weight of gallic acid, wherein the content of (a), which is available in a concentration of 2 percent by weight linked to a microcapsules, ranges from 0.1 to 10 percent by weight;

(b) an extract of the silkworm obtained by extraction, containing the peptide Cecropine, amino acids and a vitamin mix, wherein the content of (b) may range from 0.1 to 10 percent by weight;

(c) a non-ionic, cationic or anionic hydrogel or mixture of hydrogels, wherein the content of (c) may range from 0.1 to 5 percent by weight;

(d) one or several phospholipids comprising 0.1 up to 30 percent by weight;

(e) up to 100 percent by weight of water related to the total weight of the active substance preparation each.

As applicable, the active substance preparation may also contain:

(f) an ultrasound decomposition product of a yeast containing 15 at least 150 units of superoxide dismutase per ml, wherein the content of the decomposition product (f) is in the range from 0 to 4 percent by weight;

(g) an extract of acerola fruits *Malpighia punidifolia*, wherein the content (g) is in the range from 0 to 20 percent by weight; and (h) a mixture of 0.1 percent by weight of liposomal *Micrococcus luteus* extract, retinyle palmitate and tocopherylacetate prepared with phospholipids and free retinyle palmitate related to the total weight of the active substance preparation each.

For one embodiment of the invention comprising the active substance component (h) the portions of the preparation related to the total weight of the cosmetic are as follows: capsules of the active substance according to (a) ranging from 0.1 to 10 percent by weight, hydrogel according to (b) ranging from 0.1 to 5 percent by weight, encapsulated retinyle palmitate according to (h) 0.001 to 5 percent by weight, encapsulated tocopherylacetate according to (h): 0.001 to 2 percent by weight free retinyle palmitate according to (h): 0.1 to 5 percent by weight, phospholipids: 0.2 to 5 percent by weight, water as the remaining portion up to 100 percent by weight and/or other auxiliary or carrier substances.

The Quebracho bark extract according to the invention or its hydrolysis product has a very high portion of proanthocyanidines representing condensed tannins. These compounds appearing as oligomers and the low portion of gallic acid in this combination and in a concentration between 1 and 10 percent by weight shows a clear radical protection effect, which by far exceeds the effect of superoxide dismutase (SOD). The activity against free radicals was compared with that of SOD and found to be 42% for a 1 percent by weight solution of the extract (SOD 4%), 83% for a 2.5% by weight solution (SOD 15%)and 100% for a 5% by weight solution (SOD 38%). Preferably the extract (a) contains at least 95 percent by weight of proanthocyanidine oligomers and up to 5 percent by weight of gallic acid, in particular at least 99 percent by weight of proanthocyanidine oligomers and up to 1 percent by weight of gallic acid.

The content of (a) is 1 to 10 percent by weight, wherein the active substance from the Quebracho bark is enclosed in microcapsules. The microcapsules may consist of petrolatum, sodium tristearat, agar, phenonip and water.

The silkworm extract (b) is obtained by extraction of the silkworm (*Bombyx mori*) with 1,2-propylene glycol and contains vitamins, amino acids and the Cecropine peptide, which has a special antibacterial functionality. A range of studies of the haemolymph and the cuticular matrix of the silkworm carried out during the last years showed that it does not only contain antibacterial peptides but also inhibitors, in particular fungal protease inhibitors. Such extracts also show oxygen consuming properties, thus activating the cellular metabolism, and they have moisture-keeping properties, a clear curative effect on lesions in the skin by reducing healing time and a skin-smoothing effect.

Preferably, the extract (b) includes the amino acids aspertinic acid, asparagine, threonine, serine, glutaminic acid, praline, glycine, alanine, valine, cysteine, methionine, isoleucine, leucine, tyrosine, phenylalanine, lysine, histidine, arginine.

Preferably extract (b) also contains a vitamin mixture including vitamins $B_1$, $B_2$, $B_5$, $B_6$, $B_8$, $B_9$, $B_{12}$, PP, A, E and C.

The concentration of components (a) and (b) in the active substance preparation preferably ranges from 0.1 to 3 percent by weight each, in particular from 0.5 to 3 percent by weight. The gel contained according to the invention, which may also be a mixture of different gels, is a hydrogel soluble in water at temperatures above 40 up to 50° C., approximately, and which takes the gel structure at low temperatures between 10 and 30° C. Examples of such gels are non-ionic polymers such as polyvinyl alcohol, polyvinyl pyrrolidone-modified maize starch and hydroxyethylcellulose, cationic polymers such as cationic Guar, cationic cellulose, synthetic cationic polymers or gels such as gelatine, carrageenan, bentonite gels, copolymeric gels such as carbomer.

The phospholipids contained according to the invention have been selected among phosphatidyl choline, phosphatidyl ethanolamine, phosphatidyl inositol, phosphatidyl serine, phosphatidic acid and lysolecithines as well as mixtures thereof. Known products are Phoslipone, for example. The contents of phospholipids ranges from 0.1 to 30 percent by weight, preferably 0.5 to 20 percent by weight.

The components (a) and (b) of the active substance preparation and the phospholipids (d) presumably form association-like configurations of different molecules which again are accumulated mostly homogeneously in the generating structure of the gel (c)+(e), the whole being called "association complex". This may also include portions of the SOD-containing yeast decomposition product and of the acerola extract as well as certain plant extracts.

The encapsulated mixture of 0.1 percent by weight of *Micrococcus luteus* extract, retinyle palmitate and tocopherylacetate is present as liposome prepared with phospholipids, wherein the content of retinyle palmitate and tocopherylacetate may preferably range from 0.001 to 1 percent by weight. The portion of phospholipids in this encapsulated mixture generally ranges between 5 and 40 percent by weight.

Additionally, the preparation of the active substance as an association complex may contain a mixture of the vitamins A, B and C as well as additional SOD and/or extracts of acerola fruits. However, the complete preparation of the cosmetic preparation may also contain vitamins and other antioxidants.

According to the invention, the active substance preparation may also contain, in addition to the basic components (a) through (e), different plant extracts such as citrus peel or leaf extracts (*Citrus bigaradia, Citrus hystrix, Citrus aurantifolia, Citrofurtunella microcarpa, Citrus aurantium, Citrus reticulata*), petitgrain extract (peel or fruit), extract of the Spanish cherry, kiwi extract (*Actinidia chinensis*), papaya fruit- extract (*Caricae papayae*), tea extract [leaves of green or black tea, leaves or bark of new jersey tea (*Ceanthus velutinas*)], coffee bean extract (INCI name: coffee bean extract; of green or roasted beans), prunus extract (*Prunus armeniaca, Prunus dulcis, Prunus persica, Prunus domestica, Prunus spinosa, Prunus serotina, Prunus virginiana*), extracts of the bark of the Mexican skin tree (*Mimosa tenuiflora*), angelica root extract (*Angelica archangelica*). Such plant extracts are commercially available, e.g. from DRAGOCO, Holzminden; Germany.

The content of these plant extracts may range from 0 to 40 percent by weight, preferably from 0.1 to 40 percent by weight, in particular 0.5 to 20 percent by weight, where the mixture may also contain mixtures of these extracts as well as mixtures with the components (f) and (g) of the active substance preparation.

Depending on the plant and the added quantity, the addition of the above plant extracts may increase the radical protection factor several times, presumably with the occurrence of synergistic interactions, the correlation between which we have not been able to find out yet completely.

The antioxidants that may be used in the invention include vitamins such as vitamin C and derivatives of it, such as ascorbylacetates, phosphates and palmitates; vitamin A and its derivates; folic acid and its derivates, vitamin E and its derivates, such as tocopherylacetate; flavones or flavonoides; amino acids such as histidine, glycine, tyrosine, tryptophan and derivates of it; carotinoids and carotenes, such as 13-carotin, ct-carotin; uric acid and derivates; a-hydroxy acids such as citric acid, lactic acid, malic acid; stilbenes and their derivates etc.

Vitamins may also be contained in a mixture with enzymes as another portion in the active substance preparation or in the cosmetic composition apart from the active substance preparation. The content may be at least be 0.5 percent by weight of a mixture of enzymes and vitamins containing at least 150 units/ml (U/ml) of superoxide dismutase (SOD).

Preferably, the used mixture of enzymes and vitamins is an ultrasound decomposition product of a yeast, where the decomposition product contains SOD, protease, vitamin $B_2$, vitamin $B_6$, vitamin $B_{12}$, vitamin $D_2$ and vitamin E. Preferably, it contains at least 150 U/ml of SOD, protease and the vitamins B and D, where the proportion between SOD and protease as international units at least ranges from 3:1 to 8:1.

Of special advantage for making the enzyme/vitamin mixture is an ultrasound-based decomposition method described in DE 4241154C1, where a cellular dispersion or suspension is passed through a continuous ultrasound irradiation cell, where the sonotrode protects up to half or two thirds of its length into the cell and is submerged in the medium to be exposed to ultrasound-irradiation. The sonotrode has an angle of 80.5 to 88.5 degrees, and the correlation between the submerged length in mm of the sonotrode and the exposed volume in ml is set to a value ranging from 1:1.1 o 1:20. The portion of solid particles in the medium to be exposed to acoustic irradiation ranges from 1:0.02 to 1:2.2 percent by weight.

Yeasts such as baker's yeast, brewing yeast, wine yeast as well as specially treated yeasts such as SOD-enriched yeasts can be used as cellular dispersions. For instance, a cellular dispersion that can be preferably used may contain *Saccharomyces cerevisiae*.

The addition, for instance, of 1 percent by weight of such a yeast decomposition product of baker's yeast as an optional portion of the association complex may nearly double a radical protection factor, which itself is high already, from 1620 to 3150. Further remarks on the radical protection factor will be made below. In addition to the above components the active substance preparation in the form of the association complex may also contain an extract of acerola fruits (*Malpighia punidifolia*). Acerola is a small tree indigenous to the West Indies, to northern South America, to Central America, Florida and Texas, which is rich in vitamin C and other active substances such as Vitamin A, thiamine, riboflavine and niacine, which may develop a complex activity together with different other components such as phosphor, iron, calcium. The aqueous acerola extract is normally available as a powdered product. As another active substance in the complete composition of the cosmetic preparation and in addition to the above active substance complex an especially preferred embodiment may contain one or several of the following components:

(1) extracts or treated extracts of plants binding free radicals or moisture, selected among acerola fruits (*Malpighia punidifolia*), Camellia oleifera, Colunsonia canadensis and Hibiscus sabdariffa;

(2) extracts or treated extracts of algae binding free radicals or moisture, selected among omega plankton with a high content of cerebrosid stimulants, micro algae of the chlorella species and macro algae of the ulva species associated with byssus (mussel silk) as biotechnological protein fraction and subsequently associated with dextrine, wherein the product appears in the mixture with peptide derivates derived from a-MSH and associated with xanthin.

(3) natural and synthetic polymers selected among chitosanglycolate, condensed products of desiccated milk, and activated fatty acids, (4) magnetically hard single crystals of bariumhexaferrite having a coercitive field strength of 3000–5000 Oe and a grain size of 50–1200 nm intercalated in or mixed with asymmetric lamellar aggregates for phospholipids and fluorocarbons as well as (5) other active substances and carriers selected among hyaluronic acid, omega CH activator, behentrimonium chloride, passion flower oil as well as modified kaolin.

The mentioned modified kaolin is contained according to WO96/17588 and has been modified with spherical $TiO_2$ or $SiO_2$ particles having a size of <5 $\mu$m, wherein the spherical particles's share in the kaolin mixture ranges from 0.5 to 10 percent by weight. This is what makes the preparation feel very smooth on the skin and gives it additional anti-inflammatory functionality. The modified kaoline may amount to a content ranging from 0.1 to 6 percent by weight of the total quantity of the cosmetic.

The mentioned magnetically hard particles for stimulating the circulation of the blood may be such as described in WO95/03061 or such with smaller particle sizes and in a mixture with asymmetric lamellar aggregates charged with oxygen up to the saturation pressure, where the content of magnetic particles related to the total composition of the cosmetic may range from 0.01 to 10 percent by weight.

The mentioned asymmetric lamellar aggregates are known from WO94/00098 and consist of phospholipids and fluorocarbon charged with oxygen or a fluorocarbon mixture. The fluorocarbon content is in the range from 0.2 to 100 percent by weight/volume, wherein the phospholipid has a phosphatidyl choline content of more than 30 up to 99 percent by weight and where these aggregates have a skin penetration depending on the critical solubility temperature of the fluorocarbons.

In addition, the aggregates may also appear alone in the cosmetic preparation only charged with oxygen. The content may range from 2.5 to 20 percent by weight of the total composition of the cosmetic.

These aggregates are oxygen carriers and allow the penetration of the oxygen into the skin, thus improving oxygen supply to the skin.

The preparation according to the invention further contains cosmetic auxiliary substances and carriers as normally used in such preparations, e.g. water, glycerine, propylene glycol, preserving agents, colorants, pigments with colouring effect, thickeners, softening substances, moisture-preserving substances, aromatic substances, alcohols, polyalcohols, electrolytes, polar and non-polar oils, polymers, copolymers, emulsifiers, waxes, stabilisers, tinted plant extracts such as fat-soluble gardenia extract, fat-soluble carrot extract, paprika LS extract, B-carotene, lithospermum extract and active deodorants.

It is also advantageous to add suitable water-soluble and/or oil-soluble UVA or IVB filters or both to the composition according to the invention. Among advantageous oil-soluble UVB filters are 4-aminobenzoic acid derivates such as the 4-(dimethylamino) benzoic acid (2-ethylhexyl) ester, ester of the cinnamic acid such as the 4-methoxycinnamic acid (2-ethyl-hexyl)ester, benzophenone derivates such as 2-hydroxy-4-methoxybenzophenone, 3-benzylidene camphor derivates such as 3-benzylidene camphor.

Water-soluble UVB filters are for instance sulfonic acid derivates of benzophenone or of 3-benzylidene camphor or salts such as the Na or K salt of the 2-phenylbenzimidazol-5-sulfonic acid.

UVA filters include dibenzoylmethane derivates such as 1-phenyl-4-(4'-isopropylphenyl )propane-1,3-dione.

Preferred solar radiation protection filters are inorganic pigments on the basis of metal oxides such as $TiO_2$, $SiO_2$, $ZnO$, $Fe_2O_3$, $ZrO_2$, $MnO$, $Al_2O_3$, which can also be used as a mixture with each other or with organic filters. Particularly preferred inorganic pigments are agglomerated substrates of $TiO_2$ and/or $ZnO$, having a contents of spherical and porous $SiO_2$ particles, wherein the $SiO_2$ particle size ranges from 0.05 $\mu$m to 1.5 $\mu$m and where apart from the $SiO2$ particles there are inorganic particle-type substances of a spherical structure, where the spherical $SiO_2$ particles form defined agglomerates with other inorganic substances having a particle size ranging from 0.06 $\mu$m to 5 $\mu$m.

Particularly advantageously used $SiO_2$ particles are highly monodisperse, non-porous, spherical $SiO_2$ particles according to DE 3616133, produced by hydrolytic polycondensation of tetraalkoxy silane in an aqueous alcoholic-ammoniacal medium, where a sol of primary particles is generated, which subsequently brings the contained $SiO_2$ particles to the desired particle size of about 0.05 up to 10 $\mu$m by continuously adding tetraalkoxy silane proportioned in a controlled way, depending on the reaction.

Pigments, pigment mixtures or powders with pigment-like functionality, also comprising those having a pearlescent effect, may also comprise substances such as: mica, kaolin, talcum powder, mica-titanium oxide, mica-titanium oxide-iron oxide, bismuth oxychloride, nylon globules, ceramic globules, expanded and non-expanded synthetic polymer powders, powdery natural organic compounds such as pulverized hard algae, encapsulated and non-encapsulated cereal starches and mica-titanium oxide-organic dye.

Normally, a wide range of compounds may be used as softeners, such as stearyl alcohol, glyceryl monoricinoleate, glyceryl monostearate, 1,2-propanediol, 1,3-butandiol, cetylic alcohol, isopropyl isostearate, stearic acid, isobutyl palmitate, oleyl alcohol, isopropyl laurate, decyloleate, 2-octadecanol, isocetylic alcohol, cetylic palmitate, silicon oils such as dimethylpolysiloxane, isopropyl myristate, isopropyl palmitate, polyethylene glycol, lanoline, cacao butter, vegetable oils such as maize oil, cotton seed oil, olive oil, mineral oils, butyl myristate, palmitic acid etc.

Cosmetic preparations with the preparation of the active substance according to the invention may exist as O/W or W/O emulsions. Suitable emulsifiers for O/W emulsions are for instance addition products of 2–30 mol ethylene oxide to linear $C_8$–$C_{22}$ fatty alcohols, to $C_{12}$–$C_{22}$ fatty acids and to $C_8$–$C_{15}$ alkylphenols; $C_{12}$–$C_{22}$ fatty acid monoesters and diesters of addition products of 1–30 mol ethylene oxide to glycerine Glycerine monoesters and diesters as well as sorbitan monoester and diester of $C_6$–$C_{22}$ fatty acids, polyol- and polyglycerinester; addition products of ethylene oxide to castor oil; betaines such as coconut alkyl dimethyl ammonium glycinate or coconut acylaminoethylhydroxyethylcarboxymethyl-glycinate (CTFA: cocamidopropyl betaines) as well as ampholytic tensides.

Suitable emulsifiers for W/O emulsions are for instance addition products of 2–15 mol ethylene oxide to castor oil, esters of $C_{12}$–$C_{22}$ fatty acids and glycerine, polyglycerin, pentaerythrite, sugar alcohols (e.g. sorbite), polyglucosides (e.g. cellulose), polyalkylene glycols, wool alcohols, copolymers of polysiloxan polyalkyl polyether.

The water content of a preparation with the active substance complex may vary within a wide range and is preferably between 5 and 90 percent by weight, where a lower water content of about 0.5–8 percent by weight may be found in particular in lipsticks.

The especially preferable cosmetic preparation with the active substance component (f) is a particularly effective protection against the attack of free radicals on the skin both alone and in combination with other active substances and has a surprising effect on the opening of the pores of the skin, similar to the effect of a cleaning means (peeling). This increases the efficiency of other properties by further ingredients of the cosmetic preparation, like improved moisturizing and smoothing of the skin, thus improving even more and for a longer time the entire state of the skin.

It was also surprising that the retinyle palmitate in both encapsulated and in non-encapsulated form is effective in the upper and lower layers of the skin at the same time and maintains this effectiveness over a longer period of time, thus improving the repair effect of the association complex. The latter seems to be due to the presence of tocopherylacetate, since only in this combination the simultaneous and lasting effect could be observed.

The preparation of the active cosmetic substance according to the invention, when applied either alone or in combination with other active substances, protects the skin in a particularly efficient way against the attack of free radicals on the skin. It has a high radical protection factor between 100 and $3500 \times 10^{14}$ Radicals/mg.

The radical protection factor (RPF) determines the activity of a substance for binding free radicals as compared with a test substance. The test substance consists of a highly reactive, semi-stable radical, which reacts with all known antioxidants. Such radicals include nitroxides such as proxo (2,2,5,5-tetramethyle-l-dihydropyrrolinoxy-nitroxide), tempol (2,2,6,6-tetramethyl-1-piperidinoxy-4-ol-nitroxide), DTBN (ditert-butyl-nitroxide) or preferably DPPH (1,1-diphenyl-2-picryl-hydrazyl).

The RPF is determined by measuring the signal amplitude of the test radical by electron spin resonance (ESR/EPR) before and after mixing with an antioxidant and by calculating the RPF on this basis. For a series of standard antioxidants the RPF is a known parameter, so it is 827 for all-trans-retinole, 196 for all-trans retinal acetate, 41200 for DL-α-tocopherol and about 48 for a-tocopherol acetate, each $\times 10^{14}$ radicals/mg.

The preparation of the active cosmetic substance alone, if existing as "association complex" of the components (a) through (e) and in a concentration of 10 percent by weight of (a) and (b) each has an RPF of 1255, which is very high as compared with common active substances in cosmetic formulations with declared radical scavengers, which achieve values of about 4 to 40. This is the case even though the concentration of the active substances themselves in (a) and (b) is only 2 percent by weight, as a maximum. "High radical protection factor" according to the present invention means a value of 100 or higher, preferably 1000 or higher. In certain combinations of plant extracts and the association complex itself according to the present invention this value may be increased to 10000 and higher. Depending on the portion of the preparation, the corresponding cosmetic compositions with such preparations comprise radical protection factors, for example, from 40 to 200 or higher. The exact method for measuring the radical protection factor has been described by Herrling, Groth, Fuchs and Zastrow in Conference Materials "Modern Challenges To The Cosmetic Formulation" 5.5.-7-5.97, Düsseldorf, p. 150–155, Verlag f. chem. Ind. 1997. Starting from the known concentration of the test substance (here: DPPH) or the number of its free radicals (radicals per ml) they measure a signal amplitude $S_1$ with an ESR spectrometer. The test radical and the antioxidant are dissolved in a water/alcohol solution (e.g. 0.1 m) each. The signal amplitude $S_2$ of the antioxidant is measured. The normalised difference between the two signal amplitudes is the reduction factor RF.

$$RF = (S_1 - S_2)/S_1$$

The result of the radical reduction of the test substance RC ×RF is normalised relative to the quantity of product input PI (mg/ml). Where RC is the amount of the test substance, i.e. the known number of radicals in the test substance. The radical protection factor is calculated by means of the following equation:

$$RPF = \frac{RC \ [\text{Radicals/ml}] \times RF}{PI \ [\text{mg/ml}]}$$

The result is $$RPF = N \times 10^{14} [\text{Radicals per mg}],$$

where N is a positive real number and RPF for simplification may be reduced to the value of N. This reduction has been used in the examples of the present invention.

The radical protection factor may be determined by means of a handy and very simple ESR spectrometer (GALENUS GmbH, Berlin, Germany) and is a new magnitude for characterising cosmetic products as regards their capacity of binding free radicals. The method is an in vitro method, where no individual properties of the user of the cosmetic are influencing the antioxidants.

Other advantageous effects of products with the active substance preparation according to the invention, in combination with other active substances or carriers are a lasting improvement of the general state of the skin, a delayed ageing process of the skin, lasting improvement of the moisturizing and smoothing effect on the skin. The particularly advantageous embodiment described above with an additional algae-peptide product and magnetically hard single crystals of bariumhexaferrite comprises a special allergy-reduced risk, according to allergy and dermatological tests.

The cosmetic preparation according to the invention may be used, for example, in sun creams, sun gels, after-sun products, day creams, night creams, masks, body lotions, cleansing milk, makeup's, lipsticks, eye cosmetics, hair masks, hair conditioners, shampoos, shower gels, shower oils, bathing oils and other common products. A particular advantage of the active substance preparation according to the invention is the embodiment with the optional component (f) in a cream, lotion, a makeup, fluid, gel or lipstick. Advantageous cosmetic preparations also include tooth pastes mouthwash, under the special aspect of neutralising free radicals in the mouth of smokers and also as special cream for the hands and the face of smokers. Such products are manufactured in a way known by workers skilled in the art. When selecting special carrier substances, the corresponding pharmaceutical preparations may also be made.

Another subject matter of the invention is a cosmetic preparation comprising a content of plant extract selected from the group comprising citrus extract, petitgrain extract, cherry extract of the Spanish cherry, papaya fruit extract, tea extract, coffee bean extract, prunus extract, skin tree extract, angelica extract and mixtures of them as has been defined more in detail above, with a content of 0.5 to 40 percent by weight as well as 99.5 to 60 percent by weight of other active substances or carriers or mixtures of active substances and carrier substances, each related to the total composition. Active and carrier substances may be the substances mentioned above.

The following examples are to illustrate the invention more in detail. If not otherwise indicated, all measures will be given in percent by weight.

Manufacture of the Active Substance Complex

For making the gel basis, gel powder such as carbomer was added to water, homogenised and subsequently neutralised with triethanolamine, for example. Then ethanol and glycerine were added to improve mixing properties, and the mixture was well stirred.

To this gel basis a mixture of phospholipids (Phoslipone), Quebracho extract and silkworm extract was added and mixed at a temperature of up to 45° C. Then another portion of the above gel or a second gel such as Guar propyl triammonium chloride was added and stirred well with the whole mixture at increased temperature, but below 45° C. This way you got the active substance preparation according to the invention, hereinafter called "complex".

In those cases where the active substance preparation contained other ingredients such as yeast decomposition product, acerola extract or extracts of tea, coffee, kiwi, citrus, cherry, papaya or skin tree, such extract was added to the mixture of phospholipids and mixed with the gel.

EXAMPLE 1

Day cream phase A: carbomer 0.2; glycerine 2.0; propylene glycol 1,0; dist. water q.s. ad 100;
phase B: $C_{12}$–$C_{15}$-alkyl cetylic alcohol 3,7; stearate 0,5; jojoba oil 1,0;
phase C: triethanolamine 0,2;
phase D: active substance complex with (a) through (f) 3.5 perfume 0.5; preservant 0.3

Phases A and B were warmed up to 65±2° C. while being stirred, and phase B was homogenised in phase A. Then phase C was added and homogenised correspondingly. Subsequently, the mixture was cooled down to 35° C. while being stirred, and phase D was added and mixed thoroughly. The active substance complex contained 1.0% of an SOD-containing enzyme/vitamin product obtained from baker's yeast using the ultrasound method according to DE 4241154C1.

The added active substance complex contained 1% of dry gel, 7% of phospholipids, 2% of Quebracho extract, 1% of silkworm extract, 1% of SOD from a yeast decomposition product. The radical protection factor of this active substance complex amounted to 1925, and in the formulation the RPF was around 49.

EXAMPLE 2

Special Cream phase A: glycerine 3.0; dist. water q.s. ad 100;
phase B: Vaseline 22.5; jojoba oil 5.0;
phase C: active substance complex with (a) through (f) 5.5; asymmetric lamellar aggregates (AOCS) according to example 2 of W094/00109 10.5; AOCS with Ba hexaferrite single crystals according to example 1 of W095/03061, 2.0; modified kaolin according to example 1 of W096/17588 0,3.

Phases A and B were warmed up to 65±2° C. while being stirred, and phase B was homogenised in phase A. Subsequently, the mixture was cooled down to 35° C. while being stirred, and phase C was added and mixed thoroughly.

The active substance complex contained 1.0 % of an SOD-containing enzyme/vitamin product obtained from wine yeast using the ultrasound method according to DE 4241154C1 and in addition 0.5% of vitamin E and 0.5% of vitamin C. The basic ingredients of the active substance complex were 0.5% of dry gel, 10% of phospholipids, 1% of Quebracho extract, 2% of silkworm extract. The radical protection factor of this active substance complex amounted to 2120, and in the formulation the RPF was around 41.5.

EXAMPLE 3

Sun Gel phase A: carbomer 1.5; glycerine 3.0; propylene glycol 2.5; dist. water q.s. ad 100;
phase B: triethanolamine 1,5;
phase C: peptide preparation MAP-XE according to PCT/DE97/02941 1,0; ZnO 2.0; $TiO_2$ 5.0; $SiO_2$ 1.0; shellac (20% aqueous solution) 1.0;
phase D: active substance complex with (a) through (f) 3,5;
phase E: perfume 0.5, preservant 0,3.

Phase A was warmed up to 60±2° C. while being stirred and homogenised and cooled down to 45° C. Phase B was homogenised in phase A. After cooling down to about 40° C., phase C was added and the mixture was well homogenised. Subsequently, the mixture was cooled down to 35° C. while being stirred, and phases D and E were added and mixed and stirred thoroughly. The active substance complex contained 1.0 % of an SOD-containing enzyme/vitamin product obtained from brewer's yeast using the ultrasound method according to DE 4241154C1 and in addition 0.5 % of vitamins E, vitamin C and vitamin A, each. The basic ingredients of the active substance complex were 0.15% of dry gel, 20% of phospholipids, 5% of Quebracho extract, 3% of silkworm extract. The radical protection factor of this active substance complex amounted to 3050.

EXAMPLE 4

Day Cream

A composition according to example 1 was made, with the active substance complex containing 20% of black tea extract instead of 1% of SOD of a yeast decomposition. The radical protection factor of this active substance complex amounted to 3100.

EXAMPLE 5

Sun Cream

A composition according to example 1 was made, wherein phase A contained an additional 3% of $TiO_2$ and 7.5% of benzophenone-3. Instead of 1% of SOD of a yeast decomposition, the active substance complex contained 5% of coffee bean extract of roasted coffee beans and 2% of kiwi extract. The radical protection factor of this active substance complex amounted to 3200.

EXAMPLE 6

Day Cream

A composition according to example 1 was made, wherein phase A contained an additional 1% of $TiO_2$ and 0.5% of ZnO. Instead of 1% of SOD of a yeast decomposition, the active substance complex contained 1% of green tea extract, 2% of an extract of green coffee beans, 1% of vitamin C and 1% of vitamin E (tocopherolacetate). The radical protection factor of this active substance complex amounted to 5600.

EXAMPLE 7

Example for Comparison Purposes

The following components of an active substance complex were mixed with each other:

0.15% of guar propyl triammonium chloride (gel); 20% of phospholipids; 0.1% of triethanolamine; 1.0% of vitamin E; 0.1% of vitamin C; 78.65% of water.

The measured radical protection factor of the whole compound was 2.

EXAMPLE 8

Emulsion-based Fluid with Increased Vitamin A Content (Vitamin $A^2$)

phase A: carbomer 0.05, glycerine 2.5, propylene glycol 0,5; dist. water q.s. ad 100;

phase B: $C_{12}$–$C_{15}$-alkyl cetylic alcohol 1.5; stearate 0,1; olive oil 1,0;

phase C: triethanolamine 0,05;

phase D: complex with (a) through (d) containing 2% of quebracho extract, 2% of silkworm extract, 0.1% of carbomer, 0.1% of TEA, water 0.9%; as well as (h) retinyle palmitate and tocopherylacetate (1:1) as liposomes with phospholipids with 0.1% of *Micrococcus luteus* extract =0.1, retinyle palmitate (free) 0.5; phase E: perfume oil 0.2, preservant 0.3.

Phases A and B were warmed up to 65±2° C. while being stirred, and phase B was homogenised in phase A. Then phase C was added at about 50° C. and homogenised correspondingly. Subsequently, the mixture was cooled down to about 30° C. while being stirred, and phases D and E were added and mixed and homogenised thoroughly.

The radical protection factor of the complex amounted to 2100, and in the fluid the RPF was around 20.

EXAMPLE 9

O/W Antismoke Day Cream phase A: sorbitan monostearate 4; avocado oil 3; Oleyl oleate 8;

phase B: water q.s. ad 100; propylene glycol 2, glycerine 5 carbomer 0.2;

phase B1: NaOH 0.4;

phase C: preservant 0.4;

phase D: active substance complex with (a) through (f) with vitamins A,E,C,B 5;

phase E: perfume oil 0,5.

Phases A and B were made separately at 80° C. while stirring intensively and subsequently mixed, stirred and homogenised. After cooling down to 60° C., phase B1 was added for neutralisation. After cooling down to 50° C., phase C was added. At 30° C. phases D and E were added to the mixture one after another and homogenised; RPF=39.

EXAMPLE 10

Antismoke Night Cream

The cream provides a repair effect to a smoker's skin while at the same time having a prophylactic effect for the day.

phase A: Vaseline 8.5; jojoba oil 3.0; stearic acid 3.8;

phase B: water q.s. ad 100; glycerine 5; carbomer 0.3;

phase C: triethanolamine 0,3;

phase D: preservant 0.4;

phase E: active substance complex (a) through (f) with vitamins A, E, C, B and 2% aloe vera 10.0; perfume oil 0.1.

The procedure was the same as in example 9; RPF =48.

EXAMPLE 11

Hand Cream Against Brown Smoker's Fingers phase A: cetylic alcohol 8.5; stearic acid 3.8;

phase B: water q.s. ad 100; glycerine 2, carbomer 0.9;

phase C: triethanolamine 0,3;

phase D: vitamin E 1.0; aloe vera 1.0; preservant 0.4; active substance complex with (a) through (f) with vitamins A, E, C 5.0; perfume oil 1.4; whitening complex 1,0.

The procedure was the same as in example 9; RPF=35.

What is claimed is:

1. Cosmetic active substance preparation with a radical protection factor, which comprises a content of
   (a) a product obtained by extraction of the bark of *Quebracho blanco* and subsequent enzymatic hydrolysis, containing at least 90 percent by weight of proanthocyanidine oligomers and up to 10 percent by weight of gallic acid, where the content of (a), in the cosmetic active substance prepartion ranges from 0.1 to 10 wt. % and wherein (a) is present as a microcapsule with a concentration of the extraction product of 2 wt %;
   (b) an extract of silkworm obtained by extraction, containing the peptide cecropine, amino acids and a vitamin mix, where the content of (b) ranges from 0.1 to 10 wt. %;
   (c) a non-ionic, cationic or anionic hydrogel or mixture of hydrogels, where the content of (c) ranges from 0.1 to 5 wt. %;
   (d) at least one phospholipid in the range of 0.1 up to 30 wt. %;
   (e) water,
   wherein the radical protection factor is in the range 100 to $3500 \cdot 10^{14}$ radicals per mg preparation; and wherein an association complex is between the phospholipids (d), at least comprising the components (a) and (b) and the gel (c) with the water (e).

2. Preparation according to 1 further comprising
   (f) an ultrasound product of a yeast containing at least 150 International units of superoxide dismutase per ml, wherein the content of the decomposition product (f) is in the range from 0.1 to 4 wt. %, and
   (g) an extract of acerola fruits *Malpighia punidifolia*, wherein the content (g) is in the range from 0.1 to 30 wt. %; related to the total weight of the active substance preparation each.

3. Preparation according to 2 further comprising
   (h) a mixture of 0.1 wt. % if *Micrococcus luteus* extract, retinyl palmitate and tocopherylacetate in liposomal form prepared with phospholipids, and additionally tree retinyl palmitate and where the portion of the components contained in the preparation relative to the total weight of a cosmetic preparation are as follows: product of (a) and extract of (b) ranging from 0.1 to 10 wt. %, hydro gel according to (c) ranging from 0.1 to 5 wt. %, encapsulated retinyl palmitate according to (h) ranging from 0.001 to 5 wt. % encapsulated tocopherylacetate according to (h) 0.001 to 5 wt. %, tree retinyl palmitate according to (h) 0.1 to 5 wt. %, phospholipids 0.2 to 5 wt. %.

4. Preparation according to claim 3, wherein the portions of the components lie within the following ranges: product of (a) and extract of (b) ranging from 0.5 to 3 wt. %, hydro gel according to (c) ranging from 0.1 to 3 wt. %, encapsulated retinyl palmitate according to (h) ranging from 0.05 to 2 wt. %, encapsulated tocopherylacetate according to (h) ranging from 0.05 to 1 wt. %, free retinyl palmitate according to (h) ranging from 0.5 to 2 wt. %.

5. Preparation according to claim 1, wherein a radical protection factor in the range from 1000 to $3500 \cdot 10^{14}$ radicals per mg measured by determining the number of free radicals of a solution of a test substance ($S_1$) by electron spin resonance (ESR) as compared with the ESR measurement result of the cosmetic active substance preparation according to the relationship $RPF=(RC \times RF)/PI$, where $RF=(S_1-S_2)/S_1$; RC=concentration of the test substance (radicals per ml); PI=concentration of the active substance preparation (mg per ml).

6. Preparation according to claim 1, wherein the product (a) contains at least 99 wt. % of proanthocyanidine oligomers and up to 1 wt. % of gallic acid.

7. Preparation according to claim 1, wherein the amino acids contained in (b) are selected from the group consisting of aspertine acid, asparagine, threonine, serine, glutamic acid, proline, glycine, alanine, valine, cysteine, methionine, isoleucine, leucine, tyrosine, phenylalanine, lysine, histidine, and arginine.

8. Preparation according to claim 1, wherein the vitamin mixture included in (b) comprises the vitamins $B_1$, $B_2$, $B_5$, $B_6$, $B_8$, $B_9$, $B_{12}$, PP, A, E and C.

9. Preparation according to claim 1, wherein the active substance preparation contains an additional mixture of the vitamins A, E and C or each of these vitamins individually.

10. Preparation according to claim 1, wherein the active substance preparation is a cosmetic composition further comprising at least one of the following components:

(1) extracts binding free radicals or moisture of
  (1.1) plants selected from the group consisting of acerola fruits (*Malpighia punidifolia*), *Camellia Oleifera, Colunsonia canadensis* and *Hibiscus sabdariffa*; or
  (1.2) algae selected from the group consisting of omega plankton, providing a high portion of cerebrosid stimulants, microalgae of the chlorella species and macro algae of the ulva species with byssus (mussel silk) as biotechnological protein fraction and subsequently associated with dextrine, wherein the product is in the mixture with peptide derivates derived from a-MSH and associated with xanthin;
(2) yeast decomposition products selected from the group consisting of baker's yeast, brewer's yeast, wine yeast and made according to an ultrasound treatment of the aqueous yeasts;
(3) natural and synthetic polymers selected from the group consisting of chitosanglycolate, condensed products of desiccated milk, and activated fatty acids;
(4) magnetically hard single crystals of bariumhexaferrite having a coercitive field intensity of 3000–5000 Oe and a grain size of 50–1200 nm intercalated in or mixed with asymmetric lamellar aggregates of phospholipids and fluorocarbons; and
(5) other active substances selected from the group consisting of chitosanglycolate, hyaluronic acid, omega CH activator, behentrimonium chloride, passion flower oil and carrier substances;
(6) mixtures thereof.

11. Preparation according to claim 1, wherein the concentration of the product (a) and extract (b) in the active substance ranges from 0.1 to 3 wt. % each.

12. Preparation according to claim 1, wherein the preparation comprises an additional portion if 0.1 to 20 wt. % of plant extracts selected from the group consisting of citrus peel or leaf extracts (*Citrus bigaradia, Citrus hystrix, Citrus aurantifolia, Citrofurtunella microcarpa, Citrus aurantium, Citrus reticulata*), petitgrain extract (peel or fruit), extract of the Spanish cherry, kiwi extract (*Actinidia chinensis*), papaya fruit extract, (*Caricae papayae*), tea extract [leaves of green or black tea, leaves or bark of tea (*Ceanthus velutinas*)], prunus extract (*Prunus armeniaca, Prunus dulcis, Prunus persica, Prunus domestica, Prunus spinosa, Prunus serotina, Prunus virginiana*), extracts of the bark of the Mexican skin tree (*Mimosa tenuiflora*), angelica root extract (*Angelica archangelica*); and the remaining portion of carrier substances.

* * * * *